US008393324B1

(12) United States Patent
Saad

(10) Patent No.: US 8,393,324 B1
(45) Date of Patent: Mar. 12, 2013

(54) DIRECTIONALLY EFFICIENT RESPIRATOR MASK

(76) Inventor: Steven Saad, Knoxville, TN (US)

(*) Notice: Subject to any disclaimer, the term of this patent is extended or adjusted under 35 U.S.C. 154(b) by 411 days.

(21) Appl. No.: 12/765,608

(22) Filed: Apr. 22, 2010

(51) Int. Cl.
*A61M 11/00* (2006.01)

(52) U.S. Cl. ......... 128/206.21; 128/205.25; 128/205.13; 128/206.22; 128/206.23; 128/206.24; 128/206.25; 128/206.26; 128/206.27; 128/206.28; 128/206.29

(58) Field of Classification Search ............. 128/205.25, 128/205.13, 206.21–206.29
See application file for complete search history.

(56) References Cited

U.S. PATENT DOCUMENTS

| 4,832,015 | A | * | 5/1989 | Nowacki et al. | ......... | 128/205.23 |
| D362,061 | S | | 9/1995 | McGinnis et al. | | |
| 5,813,423 | A | * | 9/1998 | Kirchgeorg | ............. | 128/202.28 |
| 5,944,013 | A | * | 8/1999 | Burch | ...................... | 128/205.14 |
| 6,651,661 | B2 | * | 11/2003 | Matioc | ...................... | 128/205.25 |
| 7,243,652 | B2 | * | 7/2007 | Chang | ...................... | 128/206.26 |
| D582,031 | S | * | 12/2008 | Sorensen et al. | ........ | D24/110.4 |

* cited by examiner

*Primary Examiner* — Steven Douglas

(57) ABSTRACT

The present invention provides a symmetrical face mask suitable for use with one hand that allows an operator to provide a reliable seal with the patient's face with his/her hand and arm in an anatomically favorable position for application of a user's physical strength. In general, a user may reach at an acute angle to the plane of their chest and engage the invention mask with their hand in a manner the user may shake another person's hand, i.e., with a distal portion of their radius and ulna arranged essentially vertically so that side to side motion of the hand translates to forward and rearward motion of a mask shell while a user reserves full bi-directional rotational capability of their arm for forward or rearward rotation compression of the mask shell while, at the same time, reserving full and lever-efficient, bi-directional pushing and pulling range of a user's arm for greater pressure of the mask shell to a right or left side of a user's fleshy cheek.

9 Claims, 5 Drawing Sheets

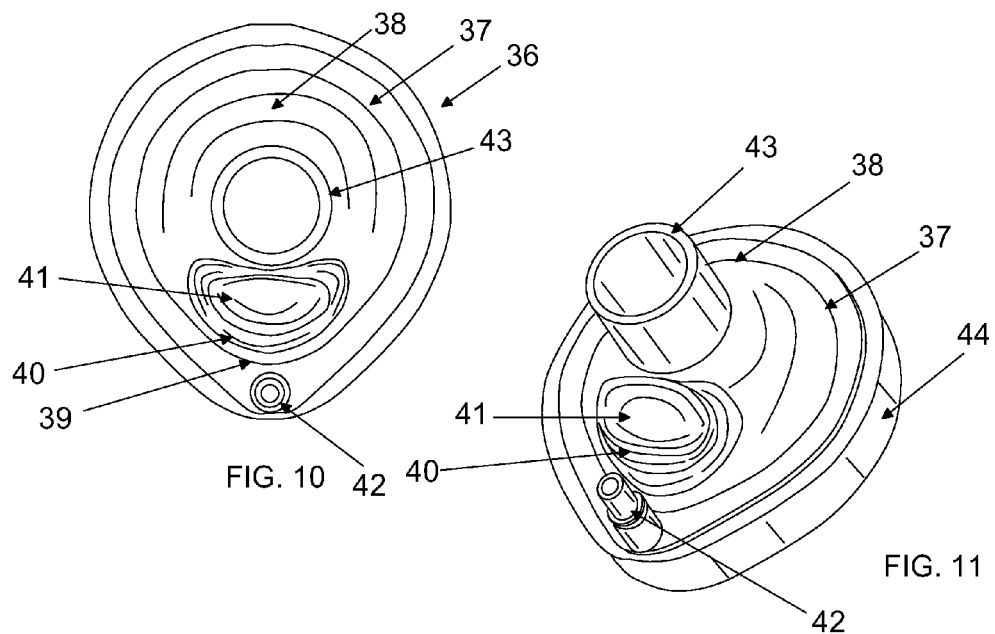
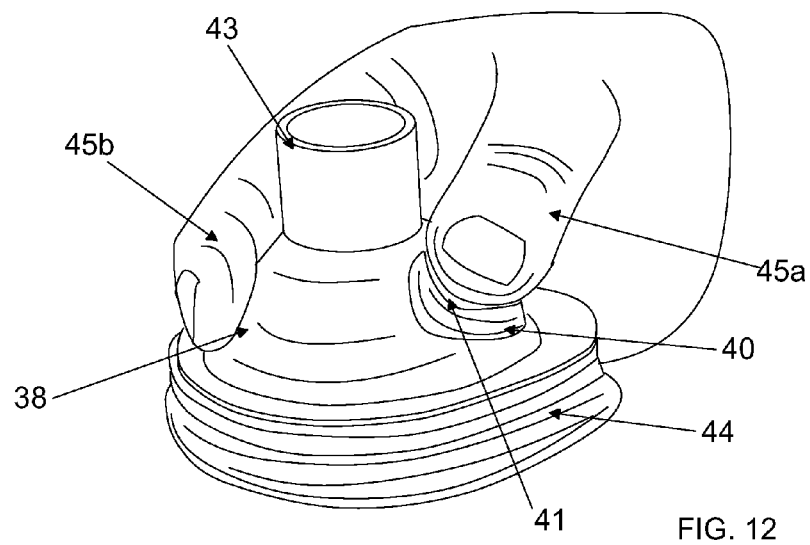

DIRECTIONALLY EFFICIENT RESPIRATOR MASK

FIELD OF THE INVENTION

The present invention relates generally to a face mask of the type used in airway management in the anesthesiology, critical care, emergency medicine and resuscitation fields, particularly relating to a mask needing a complete seal adaptable for use on both adult and child patients simply by positioning the mask and applying pressure to seal so as to be in a comfortable position for the patient and medical personnel.

DESCRIPTION OF THE PRIOR ART

A symmetrical face mask presents challenges when providing positive pressure ventilation to a patient who isn't breathing, especially when the operator has only one hand available for the mask while the other is usually squeezing a bag or getting equipment ready. Symmetrical inhalation and/or resuscitator masks which are used to provide ventilation and/or emergency resuscitation to a victim at an accident scene or in a hospital emergency room have been known in the medical field for many years. These masks typically have a relatively plyable shell and an inflatable face-contacting cushion intended for conformation to a patient's face to establish a gas tight seal inorder to deliver a volume of gas under positive pressure to a patient. The generally elongated conical shell is made from a durable flexible material such as rubber, plastic, or the like. These masks sometimes have straps which are capable of securing the mask to the face of the victim or patient. Such straps are not to be relied upon in emergency situations where sudden changes of a patient's position or condition can require the quickest of adaptations of mask to patient interface.

When positioning the mask on a patient or victim, a wider or lower end of the mask is placed proximate to the chin of the patient while a narrow end is placed on the bridge of the patient's nose. It is somewhat equivalent to impressing a saddle upon a sawhorse—there is an intimate and supportive interface between the inflatable cushion of the mask upon the bony jawbone of the chin and the conjunction of the orbital arches at the bridge of the nose. The right and left sides of the "saddle" are literally left "hanging" without support.

To the right and left sides of bony supports for the narrow upper and wide lower part of a mask (forming an axis of solid support) are fleshy, non-supportive cheek muscle and connective tissue with essentially unpredictably infinite variations of contours. The contours of the fleshy facial cheek surface and underlying muscle tone or tension results in a requirement of a sufficiently rigid mask shell so that it can support the inflatable cushion against the face of patient yet also sufficiently flexible so that medical personnel can use hand pressure to change mask shell shape to adapt the engaged inflatable cushion to the fleshy cheek portion of the patient's face.

These masks are used on children as well as adults, with the same cheek adaptation problems yet with less mask structure to manipulate, making adaptation of the mask shell's shape much more difficult. When attempting to administer a volume of gas with oxygen in order to resuscitate a child, personnel providing medical aid must select a smaller size mask.

Mask shape manipulation by medical personnel is achieved primarily by arching compression between a thumb and fingers, downward pressure resulting in flattening compression, and forward and rearward rotational compression via appropriate location of thumb and fingers upon a mask surface and as further described below.

In anesthesia, emergency medicine, critical care or resuscitation speed in achieving these adaptations is obviously critical. Positive pressure mask ventilation allows the forceful, active administration of an artificial breath and/or anesthetic gasses from a source to a non-breathing patient. Medical personnel may use a bag-mask device and hold the face mask with a left hand and squeeze the bag (develop positive pressure air flow) with a right hand. While bag-mask ventilation is a complex technique that requires considerable skill and practice, the complexity is further increased when attempting to provide a good mask seal to a patient's face.

One attempt to improve upon a basic, semi-flexible mask in a generally conical shape is found in U.S. Pat. No. 6,651,661, which discloses elevating a portion of the outer surface of a mask to continuously engage the U-shaped surface of a user's hand extending from a thumb tip to a forefinger tip. As described below, this elevated portion is somewhat advantageous in providing downward, flattening compression of the shell and a rather limited range of arching compression due to the fact that a user's hand is essentially prevented from being effectively applied to any surface of the mask shell but to the specific ergonomic surface provided to the user's thumb and forefinger. The '661 patent purports to improve mask application and adaptation during a "jaw thrust" maneuver, where the user's fingers must provide critical orientation of a patient's head and jaw while simultaneously maintaining mask shell adaptation.

While recognizing the difficulty of maintaining often asymmetrical forces on a symmetrical mask and the amount of strength which a user is typically expending in other tasks (airway bag compression; jaw orientation), the '661 patent does not address the matter of efficient application of a user's physical strength in favor of ergonomic comfort of a user's hand.

There is a need for an inhalation or resuscitation mask which provides the opportunity for more efficient application of all forms of mask shell compression or adaptation in an adult size or child size mask.

SUMMARY OF THE INVENTION

The present invention provides an symmetrical face mask suitable for use with one hand that allows an operator to provide a reliable seal with the patient's face with his/her hand and arm in an anatomically favorable position for application of a user's physical strength. In general, a user may reach at an acute angle to the plane of their chest and engage the invention mask with their hand in a manner the user may shake another person's hand, i.e., with a distal portion of their radius and ulna arranged essentially vertically so that side to side motion of the hand translates to forward and rearward motion of a mask shell while a user reserves full bi-directional rotational capability of their arm for forward or rearward rotation compression of the mask shell while, at the same time, reserving full and lever-efficient, bi-directional pushing and pulling range of a user's arm for greater pressure of the mask shell to a right or left side of a user's fleshy cheek. Preserving bi-directional and muscle and lever efficient range of motion of a user is critical in use of this invention mask in emergency or resuscitation circumstances, where speed and quick adaptation to changing circumstances is essential. Further, the invention mask, in improving efficiency of use of a user's physical strength, results in a user being able to provide consistent and intense care for longer periods of time without physical exhaustion.

In one aspect, the invention provides a multi-directional, multi-compressible face mask for engaging a patient's face for providing gas to the patient. The mask includes an inflatable cushion extending faceward from an outer edge or rim of the generally conical shell. A tubular connector member extends outwardly from the shell for administering a gas via a connected tube.

It is thus one object of the invention to provide a symmetrical face mask that may be gripped firmly and comfortably with one hand while maintaining a mask shell compression and/or orientation with a good sealed interface with a patient's face.

In another object of the invention, the face mask shell comprises two extensions, each having a vertical and horizontal surface upon which a user's thumb or forefinger may be impressed, providing thereby at least four alternate forms of compression and/or orientation for the invention face mask.

It is another object of the invention to provide two extensions outward from a symmetrical face mask shell separated in elevation along a forward and rear axial plane of the face mask adapted by such difference in elevation so that a user experiences a substantially vertical orientation of a distal ends of their radius and ulna when impressing upon vertical surfaces of said extensions their opposing thumb and forefinger of one hand grasping the face mask.

These and other aspects of the invention are not intended to define the scope of the invention for which purpose claims are provided. In the following description, reference is made to the accompanying drawings, which form a part hereof, and in which there is shown by way of illustration, and not limitation, preferred embodiments of the invention. Such embodiments do not define the scope of the invention and reference must be made therefore to the claims for this purpose.

BRIEF DESCRIPTION OF THE DRAWINGS

FIGS. 10 and 11 are, respectively, top and perspective views of a child's size form of the invention face mask.

FIG. 12 is the face mask of FIG. 10 applied to a child patient's face and showing a user's hand applying it thereto.

DETAILED DESCRIPTION OF THE INVENTION

The invention is now discussed with reference to the figures.

Figure 1:
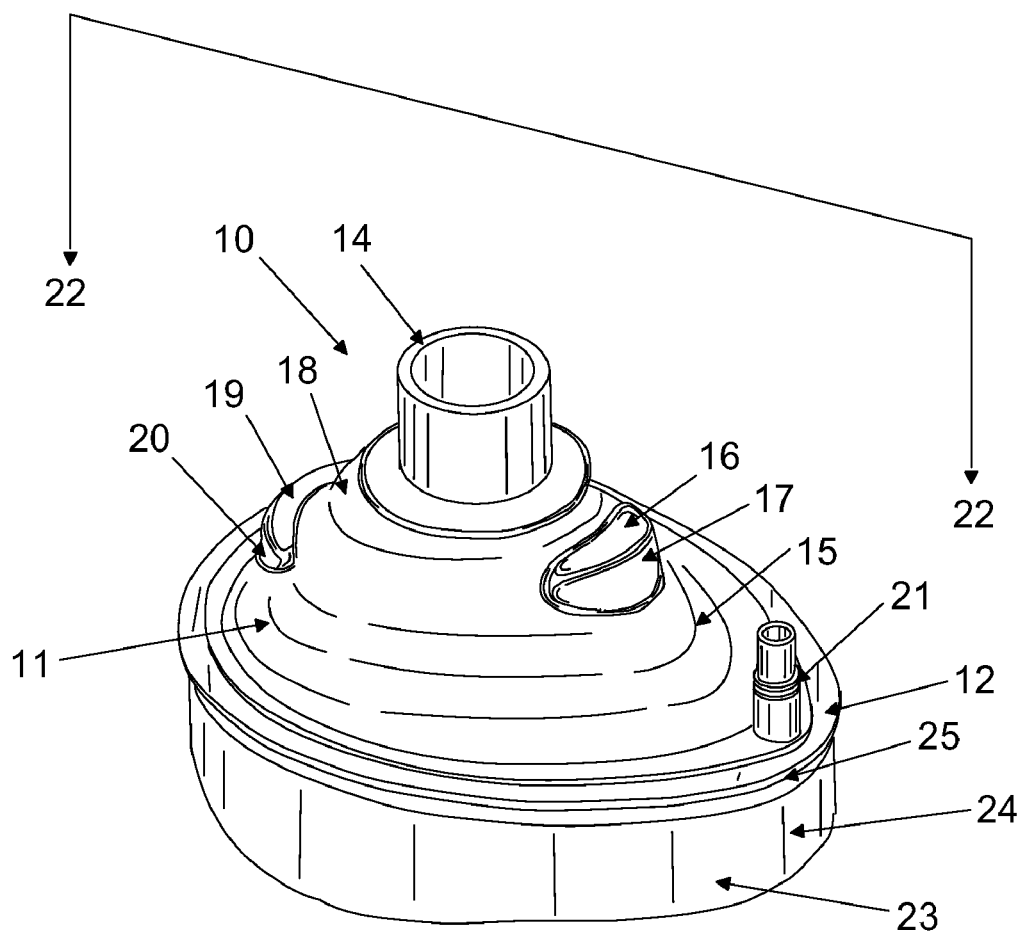
FIG. 1 is forward and side perspective view of an adult form of the invention face mask.
Figure 2:
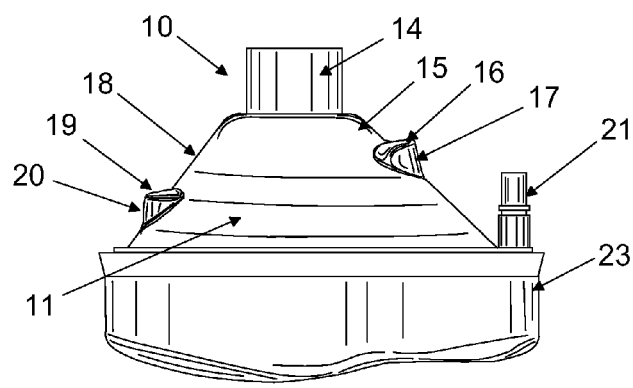
FIGS. 2, 3, 4, 5 and 6 are, respectively, right side, top, bottom, forward and rear views of the face mask of FIG. 1.
Figure 3:
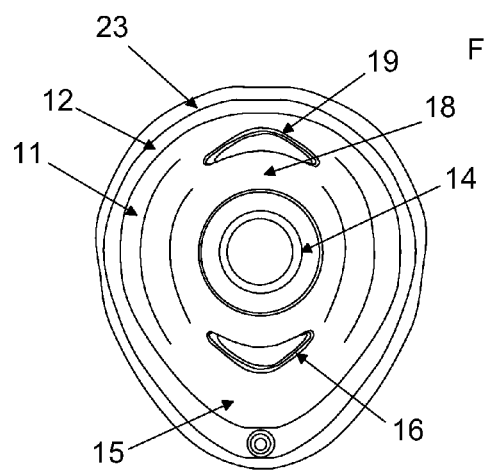
Figure 4:
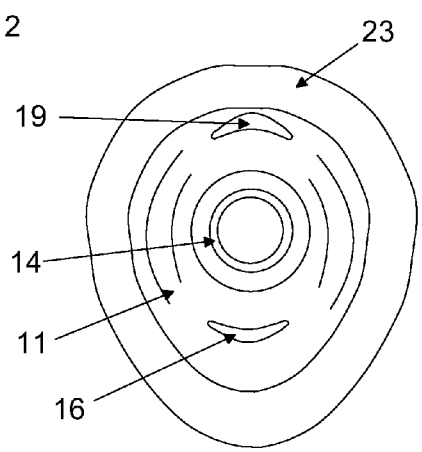
Figure 5:
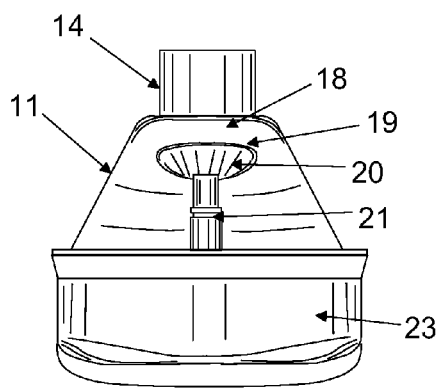
Figure 6:
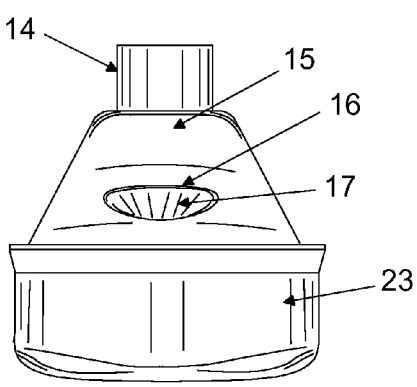

FIG. 1 shows face mask 10 comprising a generally elongated cone shell 11 extending upward to a tube connector 14 and downward to a rim 12 to which inflatable cushion 23 is connected at its upper part 25 and extending down to the flexible portion 24. An inflater stem 21 is located at a forward end of face mask 10 and is adapted to releasably inflate or deflate cushion 23, as is well known in the art.

An axial plane runs generally through shell 11 down from the section 22 lines shown in FIG. 1. Along said axial plane are located a forward surface 15 from which extends outward horizontally and vertically forward extension 16 with a top surface and a vertical surface 17. Along said axial plane are located a rear surface 18 from which extends outward horizontally and vertically rear extension 19 with a top surface and a vertical surface 20. These extensions 16 and 19 form the vertical and horizontal surfaces which enable a user to engage face mask 10 in the most efficient and effective ways to compress and/or orient face mask 10 for sealing to a patient's face. FIGS. 2 through 6 show, respectively, right side, top, bottom, forward and rear views of the face mask 10 of FIG. 1, thereby illustrating the difference in elevation of extensions 16 and 19 on shell 11.

Figure 7:
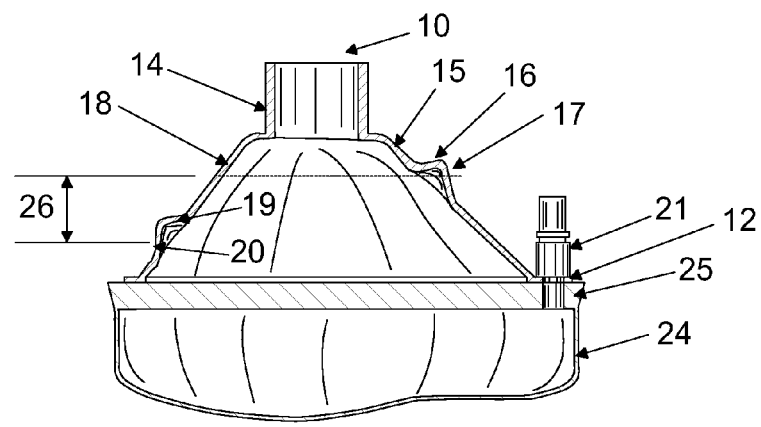
FIG. 7 is cross section 22 of FIG. 1.

FIG. 7 shows that extension 16 is located at an elevation from rim 12 substantially higher than that of extension 19. Elevation difference 26 is shown in FIG. 7 as the difference in effective contact positions for a user's thumb and forefinger, respectively, upon vertical surfaces 17 and 20. A preferred range of elevation difference 26 is from 0.25 inches to 2.00 inches, more preferably from 0.25 to 1.50 inches, and most preferably from 0.50 inches to 1.00 inch, to accommodate the hands a wide range of users to accomplish an efficient application of physical strength and user hand and arm motion range. It is preferred that an effective contact surface for a user's forefinger upon the vertical surface of extension 19 be at an elevation of from 0.25 inches to 1.5 inches, and more preferably from 0.50 inches to 1.00 inches, to accomplish the objects of the invention. The change and cost for manufacture of the invention masks in comparison to prior art masks is very small—FIG. 7 shows that extensions 16 and 19 may be formed by simple modification of existing molds for face mask shells causing a portion of the shell to be extended outward without additional polymer expended to achieve the invention face mask. The invention face mask shell 11 may be formed from polyvinylchloride of an appropriate thickness (typically above 1.5 mm), from relatively thin and flexible polycarbonate, or from other appropriate materials as may be known in the art for forming face mask shells. The face mask shell 11 of FIG. 7 is for an adult size face mask. A child size embodiment of the invention is shown in FIGS. 10 through 12.

Figure 8:
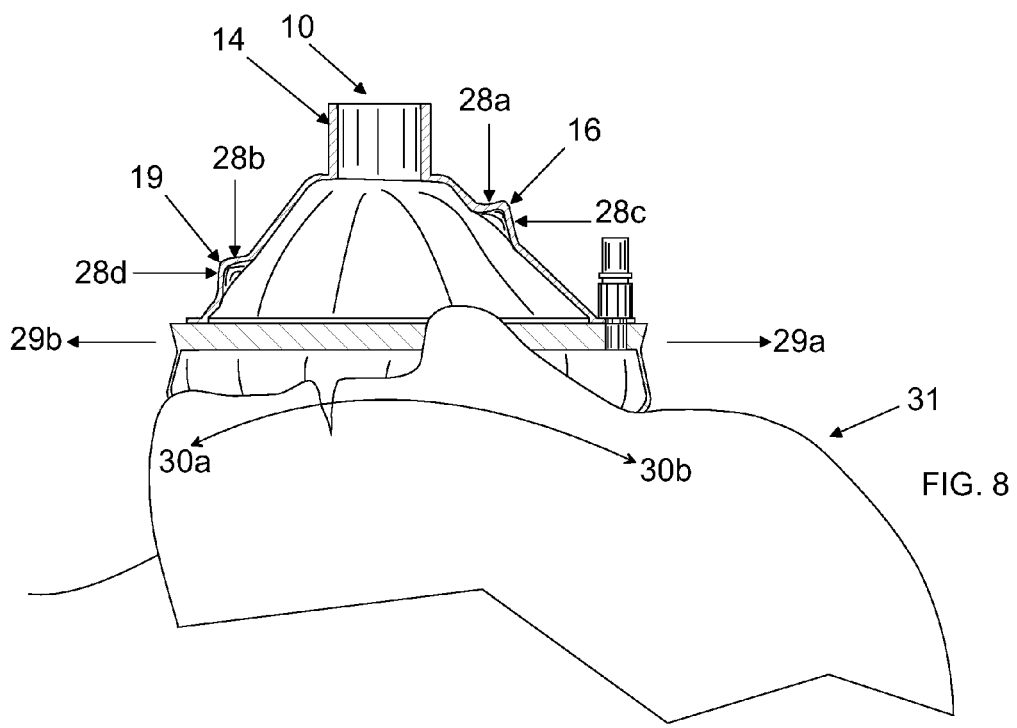
FIG. 8 is the cross section mask of FIG. 5 applied to a patient's face.

An effectively deployed face mask requires at least five basic compression and/or orientation motions which are accomplished by the invention face mask 10 through the aforementioned axial plane. FIG. 8 shows the cross section face mask 10 of FIG. 7 applied to a patient's face to illustrate those basic orientation requirements as follows:

1. Motion in direction 29a is achieved by impression in direction 28d of a user's forefinger with release of pressure in direction 28c of a user's thumb.
2. Motion in direction 29b is achieved by impression in direction 28c of a user's thumb with release of pressure in direction 28d of a user's forefinger.
3. Rotational motion in direction 30a is achieved by impression in direction 28b of a user's forefinger on a horizontal surface of extension 19 with concurrent pressure in direction 28c of a user's thumb on a vertical surface of extension 16.
4. Rotational motion in direction 30b is achieved by impression in direction 28a of a user's thumb on a horizontal surface of extension 16 with concurrent pressure in direction 28d of a user's forefinger on a vertical surface of extension 16.
5. Overall downward motion is achieved by impression in direction 28a of a user's thumb on a horizontal surface of extension 16 with concurrent pressure in direction 28b of a user's forefinger on a horizontal surface of extension 19.

These motions are not the full extent of the capabilities of a user interacting with the invention face mask. The above motions are supplemented with compression of shell 11 when a user presses in opposing directions 28c and 28d, which will arch the shell 11 to accommodate for a flatter face or one with substantial forward protrusion of the cheek areas due to natural growth, obesity, or injury. Said compression gives instantaneous and tight control over required orientations for the invention face mask. A further benefit of raising the general elevation of a user's thumb and forefinger to accomplish overall downward compression as in the fifth method above is to provide superior visualization of the periphery of cushion 23 interface with a patient's face and to provide a more sensitive control over application of such overall downward pressure, which is some cases does harm to a patient's eyes or facial injuries.

Figure 9:
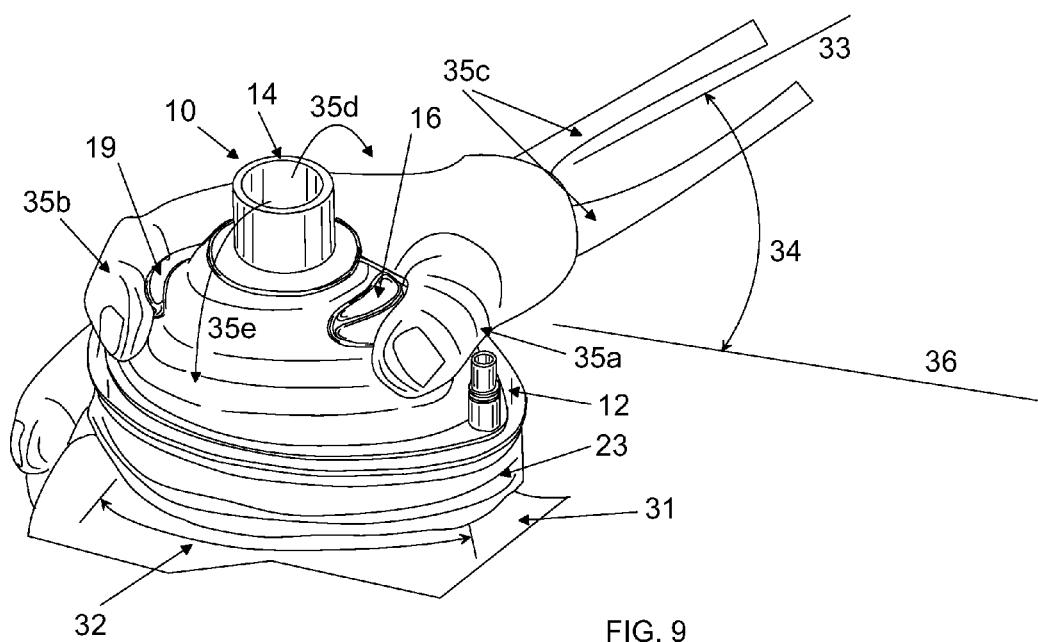
FIG. 9 is the face mask of FIG. 1 applied to a patient's face and showing a user's hand applying it thereto.

FIG. 9 shows the uses of invention face mask 10 beyond the benefits of orientations achievable along said axial plane of the shell 11 described above. The invention face mask 10 provides more efficient application of a user's physical strength and range of motion in that a user's right arm is oriented along path 33 and said axial plane in direction 35 is directed to a user's left shoulder, resulting in a substantially vertical orientation of distal portions of a user's radius and ulna bones 35*c* in a manner similar to shaking hands at such an angle 34. Placing a user's hand with thumb 35*a* engaged with extension 16 and a forefinger 35*b* engaged with extension 19 results in a user preserving a fullest range or pushing/pulling and side to side and forward and back rotational motion for a user's hand for application to the invention face mask 10 to a patient's face 31.

With a user's hand applied to the invention mask 10 as shown in FIG. 9, impression of a user's palm to rim 12 results in downward rotation 35*d* so that asymmetrical pressure is applied to the patient's right side of the face in the cheek area. With a user's thumb 35*a* applied to the top surface of extension 16 and their forefinger applied to the top surface of extension 19, the user need only press downward with thumb and forefinger and forward along direction 33 to accomplish downward rotation 35*e* so that asymmetrical pressure is applied to the patient's left side of the face in the cheek area 32. Only stable and secure elevation of a user's hand via application of thumb and forefinger to extensions 16 and 19 respectively requires such minimal outward and downward rotation of the hand to accomplish downward rotation 35*e*. Said extensions have a horizontal width equal to or less than a horizontal width of the tube connector (including the flattened area at its base part) so that a difference in the forward effective pressing elevation and the rear effective pressing elevation is adapted to provide that when a user grasps the forward extension with a thumb and the rear extension with a forefinger, said user's distal ends of their radius and ulna bones are substantially in vertical alignment and extend essentially normal to said axial plane of the shell.

FIG. 10 shows a top view of a child's size face mask 36 of the invention comprising a shell 37 with a rear portion 38 without an extension (due to small size) and a forward portion 39 with an extension 40 having a thumb concavity 41 adapted to provide a user with the ability to press down or rearward without removing the thumb 45*a*, as shown in FIG. 12, with forefinger 45*b* shown engaging shell portion 38 and capable of engaging a vertical surface of tube connector 43. The combination of the heavily concave (at least having vertical and horizontal arcuate sections along an axial plane) thumb concavity with the mask's small portion 38 adjacent to a vertical surface on the tube connector provides this child's size mask 36 with substantially similar response to a user as described for the adult mask 10 of FIG. 1 for similar motions of a user's hand and arm.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

I claim:

1. A face mask having a generally conical, symmetric shell with a narrowed, forward portion of the shell, a wider, rear portion of the shell, a tube connector at a top end of the shell and a rim peripheral to a bottom edge of the shell, which rim is sealingly connected with an inflatable cushion adapted to sealingly engage a face of a person for application of a volume of gas under positive pressure containing gases to said person, the improvement comprising a forward extension outward and upward from the shell consisting essentially of a vertical surface and a horizontal surface located on the forward portion of the shell along an axial plane of the shell and a rear extension outward and upward from the shell consisting essentially of a vertical surface and a horizontal surface located on the rear portion of the shell along an axial plane of the shell, where said extensions each have a horizontal width equal to or less than a horizontal width of the tube connector so that a difference in the forward effective pressing elevation and the rear effective pressing elevation is adapted to provide that when a user grasps the forward extension with a thumb and the rear extension with a forefinger, said user's distal ends of their radius and ulna bones are substantially in vertical alignment and extend essentially normal to said axial plane and the horizontal surface of the rear extension is adapted to receive downward pressure of a user's forefinger of a user's hand and the horizontal surface of the forward extension is adapted to receive downward pressure of a user's thumb of the same hand, whereby the vertical surface of the rear extension is adapted to receive horizontal and forward pressure of a user's forefinger of a user's hand defining a rear effective pressing elevation from said rim and the vertical surface of the forward extension is adapted to receive horizontal and rearward pressure of a user's thumb of the same hand defining a forward effective pressing elevation from said rim.

2. The face mask of claim 1 wherein a difference in the forward effective pressing elevation and the rear effective pressing elevation is from 0.25 inches to 2.00 inches.

3. The face mask of claim 2 wherein a difference in the forward effective pressing elevation and the rear effective pressing elevation is from 0.25 inches to 1.50 inches.

4. The face mask of claim 2 wherein a difference in the forward effective pressing, elevation and the rear effective pressing elevation is from 0.50 inches to 1.00 inch.

5. The face mask of claim 3 wherein rear effective pressing elevation is from 0.25 inches to 1.5 inches.

6. The face mask of claim 3 wherein rear effective pressing elevation is from 0.50 inches to 1.00 inch.

7. The face mask of claim 6 wherein said user further directs an arm for said hand in a direction at an acute angle to a chest of said user, whereby said axial plane of said shell is substantially directed to an opposite shoulder of said user.

8. A child's face mask having a generally conical, symmetric shell with a narrowed, forward portion of the shell, a wider, rear portion of the shell, a tube connector at a top end of the shell and a rim peripheral to a bottom edge of the shell, which rim is sealingly connected with an inflatable cushion adapted to sealingly engage a face of a child for application of positive pressure oxygen-containing gases to said child, the improvement comprising a forward extension outward from the shell consisting essentially of an outward extension located on the forward portion of the shell along an axial plane of the shell and defining a concavity comprising a substantial vertical surface and a substantial horizontal surface, whereby an effective rear extension of the shell consists of a rear portion the shell along said axial plane and a vertical surface along a rear portion of the tube connector, where said extensions each have a horizontal width equal to or less than a horizontal width of the tube connector so that a difference in the forward effective pressing elevation and the rear effective pressing elevation is adapted to provide that when a user grasps the forward extension with a thumb and the rear extension with a forefinger, said user's distal ends of their radius and ulna bones are substantially in vertical alignment and extend essentially normal to said axial plane and the horizontal surface of the rear extension is adapted to receive downward pressure of a user's forefinger of a user's hand and the horizontal surface of the forward extension is adapted to receive downward pressure of a user's thumb of the same hand, whereby the vertical surface of the rear extension is adapted to receive horizontal and forward pressure of a user's forefinger of a user's hand defining a rear effective pressing elevation from said rim and the vertical surface of the forward extension is adapted to receive horizontal and rearward pressure of a user's thumb of the same hand defining a forward effective pressing elevation from said rim.

9. The face mask of claim 8 wherein the concavity of the forward extension is adapted to receive downward and rearward pressure of a user's thumb of a user's hand.

* * * * *